Figure 1:
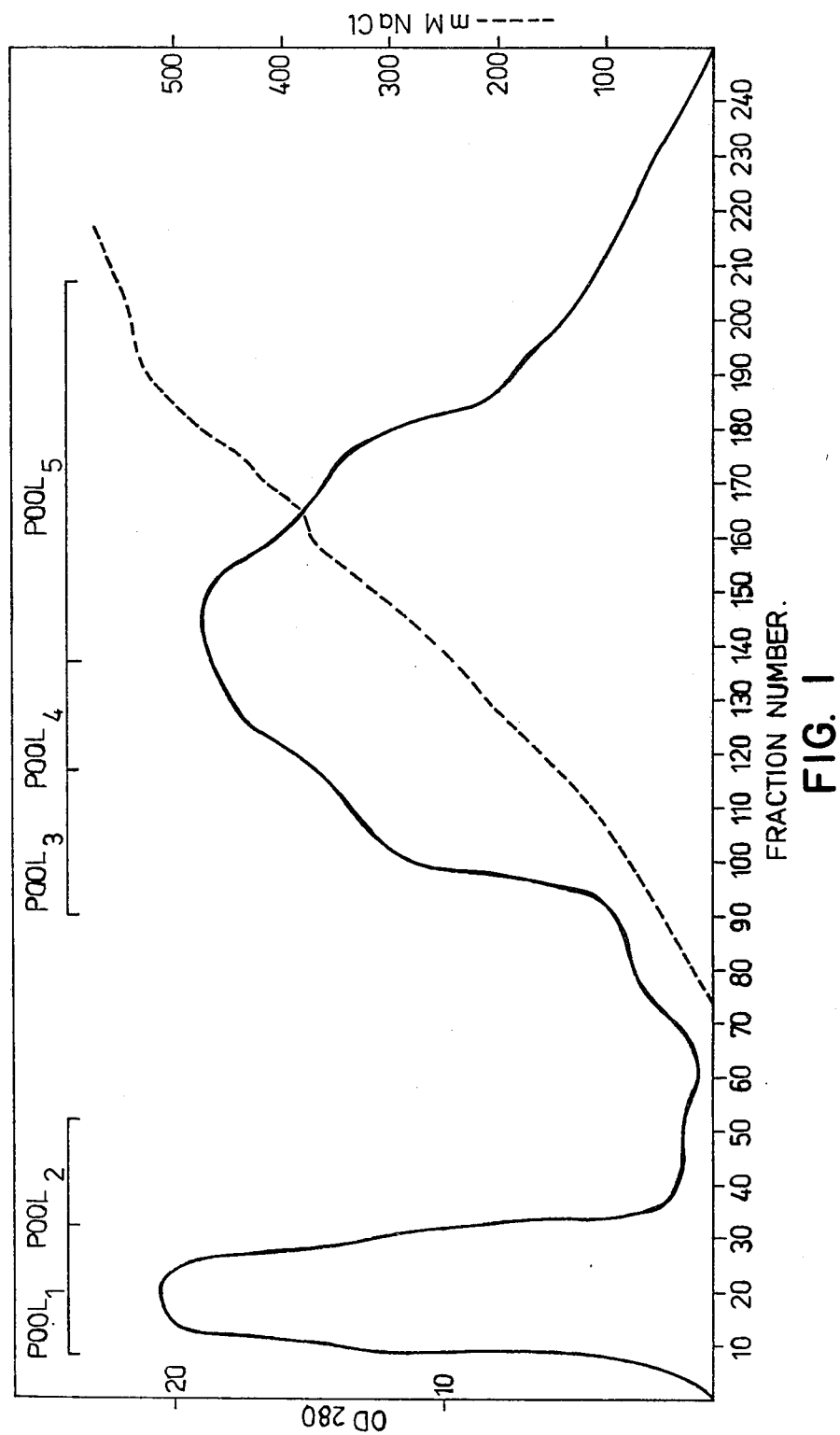

United States Patent [19]

Barbesgaard et al.

[11] 4,435,307
[45] Mar. 6, 1984

[54] DETERGENT CELLULASE

[75] Inventors: Peder O. Barbesgaard, Farum; Georg W. Jensen, Bagsvaerd; Poul Holm, Brønshøj, all of Denmark

[73] Assignee: Novo Industri A/S, Denmark

[21] Appl. No.: 256,275

[22] Filed: Apr. 23, 1981

[30] Foreign Application Priority Data

Apr. 30, 1980 [DK] Denmark .............................. 1872/80

[51] Int. Cl.$^3$ ............................................ D06M 15/02
[52] U.S. Cl. ................................ 252/174.12; 252/8.6; 252/DIG. 12; 435/209; 435/264
[58] Field of Search ........... 252/8.6, 174.12, DIG. 12, 252/DIG. 15; 435/209, 264

[56] References Cited

U.S. PATENT DOCUMENTS 3,627,640 12/1971 Blumberg et al. .................. 435/209
4,242,219 12/1980 Bogerman et al. ............. 252/174.12

FOREIGN PATENT DOCUMENTS 1368599 10/1974 United Kingdom .

OTHER PUBLICATIONS

"Cellulase of *Humicola insolens*," Ramabadran, R. Indian Journal of Experimental Biology, vol. 7(3) 1969, pp. 186–187.
"Cellulase Activity Degradation of Cellulose . . . ,"
Jain, M. K. et al., British Mycological Society, Transactions, vol. 73(1), 1979, pp. 85–89.
"Amylase and Cellulase Activities of Thermopholic . . .", Ogunders, Vincent W. Mycopathologia, vol. 69(3), 1979, pp. 131–135.
"The Role of Carbohydrate Moiety . . .", Hayashida, S. et al., Agricultural and Biological Chemistry, vol. 44(3), 1980, pp. 481–487.
Hayashida, S. et al., "Production and Purification of Thermostable . . .".
Schaumann, K., "Production and Activity of Cellulolytic Enzymes . . .".
Measurement of Cellulase, Advances in Enzymes Hydrolysis of Cellulase and Related Material pp. 85–86, 1963, Elwyn T. Reese, The Macmillan Company, New York.

*Primary Examiner*—John E. Kittle
*Assistant Examiner*—Hoa Van Le
*Attorney, Agent, or Firm*—Fidelman, Wolffe & Waldron

[57] ABSTRACT

A harshness reducing, enzymatic additive for a main wash detergent based on a fungal cellulase, i.e., a cellulase produced by means of *Humicola insolens*. The enzymatic additive can be produced in high yields and has an extraordinarily high activity at alkaline pH values, whereby it is possible to mix the additive with a main wash detergent and perform the harshness reduction and the washing as a single operation.

14 Claims, 2 Drawing Figures

DETERGENT CELLULASE

The present invention relates to improvements in or relating to a harshness reducing agent for a detergent composition, a detergent composition and a wash method.

It is known that washing of cotton-containing fabrics under normal conditions will generally cause a pronounced, unpleasant harshness in the fabric. In current laundry practice, this harshness is normally reduced by treatment of the fabrics with a softening agent (rinse conditioner) containing a cationic detergent, in a step separate from the main wash. This treatment, however, has the serious drawback that the harshness reducing effect is of a temporary nature. On the next wash the harshness will return, unless the fabric is treated once again with a softening agent. In spite of the fact that large sums of money have been spent to find better ways of reducing harshness in fabrics, the fact remains that in washing practices softening agents are added to the fabrics in a step separate from the main washing step in order to exert the full harshness reducing effect, and the harshness reducing effect is still only of a temporary nature.

There are, however, various proposals solving this problem. For example, British Patent Specification No. 1,368,599 suggests reducing harshness of cotton-containing fabrics by treatment with a cellulase. It should be noted that the treatment suggested is always conducted as a separate step, such as for example as a pre-wash or pre-soak. British Pat. No. 1,368,599 advises that cotton fabrics treated with a cellulase retain their softness for several washes. It should be noted, however, that the cellulase softening agent is not believed to be available commercially, even though this technique was known as early as 1972 (when Belgian Patent Specification No. 773,280, an equivalent of British Pat. No. 1,368,599, was published). Thus, the teaching of British Pat. No. 1,368,599 (or Belgian Patent Specification 773,280) must be treated as a theoretical possibility rather than a realistic technical teaching on which the art has been willing to commercialize.

It should be noted that bacterial cellulases are usually rather expensive, because the yield thereof is normally very small. Fungal cellulases are more promising cellulases from a commercial point of view, because these can generally be produced in rather higher yields, but fungal cellulases have poor pH characteristics for washing purposes. For example, on page 2, lines 84–90 of the Queen's printers copy of Brit. Pat. No. 1,368,599 it is stated: "Many types of cellulases derived from fungi have a pH-optimum of about 5. Above pH 7 their activity is normally greatly reduced, and therefore the cellulolytic enzymes derived from fungi should be used in the present invention in an acid medium". This means that the washing operation, which is normally carried out at an alkaline pH, cannot be carried out in the same step as the cellulase treatment. The cellulase treatment may, of course, be carried out in a first step, as an acid pre-wash or pre-soak, and thereafter the main wash carried out in a second step as an alkaline wash. As far as the inventors herein are aware there has been no disclosure in the art of any cellulase intended to be used for the performance of a washing and softening in a single step in a practical washing procedure.

Carrying out the cellulase treatment at an acid pH before the main wash necessitates the use of an intermediate rinse between the acid cellulase treatment and the main wash, unless an excess of alkali for neutralising the acidity in the cellulase treated laundry is already present in the detergent composition used for the main wash or is added thereto.

Finally, if the cellulase treating liquid contains detergents, the cleaning ability of the detergent is normally rather low at the low pH-values employed in the cellulase treatment liquid.

Thus an urgent need exists for a main wash detergent composition which contains a relatively cheap cellulase with high activity at the pH-values normally prevailing in main wash solutions.

However, the art has not identified, heretofore, any cheap cellulase which exhibits an acceptably high cellulase activity at the pH-values normally prevailing in main wash solutions in spite of the fact that a tremendous commercial advantage might be achieved if this need for such a cellulase is fulfilled.

It has now been found that a certain fungal cellulase, i.e., the fungal cellulase producible from *Humicola insolens* (*Humicola grisea* var. *thermoidea*), has a high cellulase activity at the pH-values normally prevailing in main wash solutions.

Thus, according to the first aspect of the present invention there is provided a harshness reducing agent in detergent additive form for inclusion in a detergent composition, an essential component of the additive being a fungal cellulase producible by a strain of *Humicola insolens* (*Humicola grisea* var. *thermoidea*), and wherein the harshness reducing agent is a component of a main wash detergent composition.

Expressed in another way the first aspect of this invention is use of the fungal cellulase producible from *Humicola insolens* as a harshness reducing agent in a main wash detergent composition.

It is to be understood that the fungal cellulase producible from *Humicola insolens* can be produced from regular strains of *Humicola insolens* as well as from mutants and variants of *Humicols insolens*.

By use of the harshness reducing agent for a main wash detergent composition in accordance with the invention it has become possible to perform a washing and harshness reducing process in a reasonably cheap way and in just one operation, that is, in the main wash, without any pre-soaking or other pre-treatment.

It is described in Agric. Biol. Chem 44 (3), 481–487 (1980) and 44 (8), 1721–1728 (1980) that *Humicola insolens* is a cellulase producing thermophilic fungus. Also it is described that the optimum pH's of the cellulases produced by *Humicola insolens* are 5.3 and 5.0, respectively, and this cellulase, therefore, would seem to belong to the category of acid pH cellulases discussed above in connection with British Pat. No. 1,368,599, and consequently, a cellulase unable to fulfill the purpose of the invention. Surprisingly, however, it has been found that *Humicola insolens* produces a cellulase which fulfills the purpose of the invention.

*Humicola insolens* falls within the group of thermophilic Humicola which comprises *Humicola insolens* and *Humicola* var. *thermoidea*, the taxonomic distinction between these two being very dubious.

The regular $C_x$ cellulase activity is determined by virtue of the fact that cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

The regular $C_x$ cellulase activity is determined in relation to the substrate carboxymethylcellulose (CMC Hercules, 4 M6F).

The standard conditions are the following: pH 9.50; buffer 0.1 M tris(hydroxymethyl)aminomethan ("tris"); substrate 4 g CMC/liter of the above-indicated buffer solution; incubation temperature 50° C., and incubation time 20 minutes.

One regular $C_x$ cellulase activity unit (for the sake of brevity in the following referred to as one regular $C_x$ unit) is the amount of cellulose which, under the above-indicated standard conditions, forms an amount of reducing sugar equivalent to 1 $\mu$mol of glucose per minute.

In a preferred embodiment of the harshness reducing agent according to the invention the fungal cellulase is produced by means of the *Humicola* strain DSM 1800. It has been found that this strain produces an alkaline cellulase with a high $C_x$ activity at alkaline pH values. The new *Humicola* strain has been identified at the Commonwealth Mycological Institute, Kew, England, as *Humicola insolens*. The new strain was deposited on Apr. 14, 1980 at the German Collection of Microorganisms (DSM, Deutsche Sammlung von Mikroorganismen), Göttingen, Germany, under the DSM number 1800.

The following is a morphological and physiological description of the above new Humicola strain DSM 1800.

Turf: Short, mycelium at first white, later becoming dark grey with white patches; hyphae colourless, smooth, septate approximately 2.8$\mu$ in diameter. Colourless drops of water sometimes present.

Reverse: Yellow becoming brown-dark grey with age.

Aleuriospores: Smooth; brown, produced singly, terminally on single or multicellular conidiophores; usually globose 12.6–16.8$\mu$ or sometimes subglobose 7×11.2–14×16.8$\mu$. Apiculus present.

Chlamydospores: Produced singly or in chains; smooth; brown; 11.2–16.8$\mu$.

Phialocondia: Absent.

Temperature limits: No growth at 26° C.; good growth from 37°–50° C. Colonies 8 cm in diameter at 37° C. for 5 days.

The above observations were made after 5 days at 37° C. on YPSS agar with the composition indicated below.

| | |
|---|---|
| Yeast extract Difco | 4.0 g |
| K$_2$HPO$_4$ | 1.0 g |
| MgSO$_4$.7H$_2$O | 0.5 g |
| soluble starch | 15.0 g |
| distilled water | 1000 ml |
| agar | 15.0 g |

It has been found, surprisingly, that the cellulase product produced by means of the *Humicola insolens* strain DSM 1800, besides the softening effect, exhibits a strong dirt loosening and anti-redeposition effect.

In a preferred embodiment of the harshness reducing agent according to the invention the fungal cellulase is enriched in regard to the cellulase fraction, which does not attach itself to an anion exchanger at $6.5 \leq pH \leq 7.5$.

Figure 2:
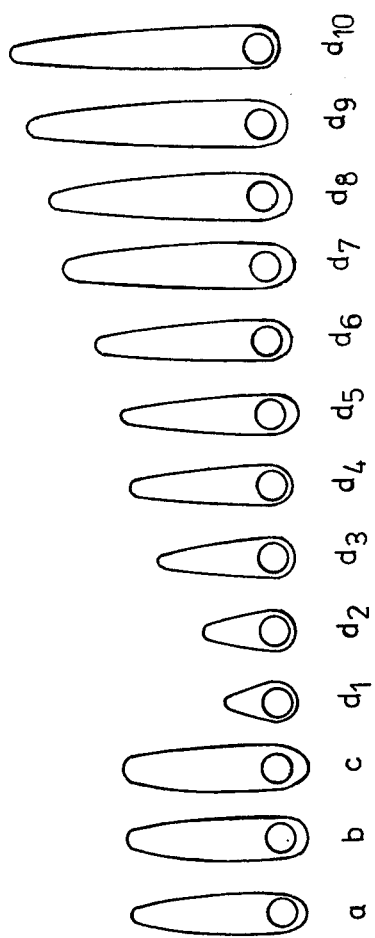

Reference is now made to the attached drawings wherein:

FIG. 1 is a graph showing the absorbance at 280 nm of the chromatographically separated fractions of the cellulase from DSM 1800; and FIG. 2 shows the results of an immunoelectrophoresis testing of the same purified cellulase fraction from different strains of *Humicola insolens*.

As will be exemplified in some detail later (vide Example 6) it has been found that the cellulase fraction, which does not attach itself to an anion exchanger at $6.5 \leq pH \leq 7.5$ (for the sake of brevity in the following referred to as the $AC_xI$ fraction) exhibits the most significant harshness reducing ability. It has also been found that the temperature stability of the $AC_xI$ fraction was better than the temperature stability of the other fractions of the *Humicola insolens* cellulase and than the temperature stability of the acid fungal cellulases described in the previously cited British Pat. No. 1,368,559.

In order to be able to ascertain the content of the $AC_xI$ fraction the modified $C_x$ (cellulase) activity may be determined in the following manner. A phosphate buffer A is made up of 26.52 g sodium dihydroxy phosphate dihydrate in 1000 ml of deionised water; thus the molarity of A is 0.17. 100 ml of A is mixed with approximately 800 ml of deionised water, pH is adjusted to 7.0 and the total volume of the buffer is adjusted to 1000 ml of buffer, this buffer being named buffer B, the molarity of which is 0.017. A column is loaded with 1 g of the anion exchanger DEAE-Sepharose Cl-6B ® and equilibrated with B. Then the enzyme is dissolved in B, and 25 ml of the thus prepared enzyme solution is passed through the above indicated, equilibrated column. The $C_x$ activity of enzyme solution downstream of the column is determined in the manner indicated above for determination of the regular $C_x$ cellulase activity. This $C_x$ activity is termed the modified $C_x$ activity and is smaller than the regular $C_x$ activity in case some $C_x$ activity is adsorbed to the anion exchanger under the condition specified.

In a preferred embodiment of the invention the fungal cellulase exhibits a ratio of $C_x$ modified/$C_x$ regular of at least 0.6, preferably at least 0.8.

It has been found that such a harshness reducing agent is enriched in regard to the $AC_xI$ fraction to such an extent that the harshness reducing ability is extraordinarily good.

In a preferred embodiment of the harshness reducing agent according to the invention, the fungal cellulase is provided as a non-dusting granulate. It is essential that the cellulase preparation has a low dust level. With a high dust level complications may arise both in factories where the cellulase preparation is mixed with detergents and during subsequent handling of the cellulase containing detergent. A granulate cellulase preparation can be prepared in a number of different ways, for example by means of a "Marumerizer" as described in British Pat. Nos. 1,362,365 and 1,361,387 or by means of a granulating machine, as described in Aufbereitungs-Technik No. 3/1970, pp. 147–153 and No. 5/1970, pp. 262–278, or it can be a prilled granulate, as described in Belgian Patent Specification No. 760.135. In all cases, however, the granulate must have low dusting properties. The word "Marumerizer" is a trademark.

In a preferred embodiment of the harshness reducing agent according to the invention, the cellulase granulate is coated with a whitening agent, preferably TiO$_2$, in combination with a dust binding agent. In this way, an attractive-looking cellulase granulate with a minimum of dusting ability is provided.

In another preferred embodiment of the harshness reducing agent according to the invention, the harshness reducing agent is in liquid form, in which instance the fungal cellulase is provided as a cellulase concentrate suspended in a solution of non-ionic surfactant. The concentrate is produced from the fermentation broth. In this embodiment, since the harshness reducing agent according to the invention is a liquid, the dust level thereof is zero, and the above-mentioned difficulties are thus avoided completely.

Advantageously, when the harshness reducing agent is a suspension, the non-ionic surfactant solution contains a thickening agent. Thereby, sedimentation of the cellulase can normally be avoided. As an example of thickening agent, fumed silica with an extremely small particle size may be used. If fumed silica is used as the thickening agent, the amount thereof is usually in the range of from 0.5 to 10 percent (w/w), preferably in the range of from 1 to 5 percent (w/w).

In the embodiments of the harshness reducing agent according to the invention wherein the harshness reducing agent is a liquid and the fungal cellulase is provided as a cellulase concentrate dissolved in an aqueous medium, preferably present is a stabilizing agent. As stabilizing agent any agent can be used which stabilizes against sedimentation and against loss of enzymatic activity.

In the second aspect of the present invention there is provision of a main wash detergent composition, which comprises detergent ingredients and the harshness reducing agent of the first aspect of the present invention in the already indicated amounts, whereby the pH of a solution of 1 g of the main wash detergent composition in 1 liter of water, with a hardness of 10° German before the addition of the main wash detergent composition, is in the range of 7 to 10, preferably in the pH range of from 7.5 to 9.5.

It is intended that the expression "main wash detergent composition" covers a detergent composition which usually, but not necessarily, is used in a single wash not preceded or followed by any other treatments of a laundry nature. The advantage associated with the main wash detergent composition according to the invention appears most clearly when the main wash detergent composition according to the invention is used in a single wash.

Selection of the detergent ingredients for a main wash detergent composition in accordance with the present invention are not critical to practice of this invention. Standard single wash detergent formulations are contemplated, the only limitation being that the ingredients therein should be compatible with the fungal cellulase.

Thus, the detergent ingredients themselves and the percentages thereof used may be the following, by way of example.

(1) Surfactants, in particular anionic and non-ionic surfactants, in a total amount of from 1 to 100 percent by weight, typically from 5 to 45 percent. Typical anionic surfactants are linear alkyl aryl sulphonates ("LAS") and α-olefin sulphonates ("AOS"). Typical non-ionic surfactants are alkyl phenyl ethoxylates and fatty alcohol ethoxylates.

(2) Builders, in particular alkaline builders, and water hardness reducers, in a total amount of from 5 to 80 percent by weight, typically from 25 to 75 percent. Typical builders are sodium tripolyphosphate ("STPP"), sodium aluminium silicates (zeolites), sodium silicates and sodium carbonates.

(3) Bleaching agents, in particular peroxides in a total amount of from 0 to 40 percent by weight, typically either 0 percent or from 15 to 30 percent. Typical bleaching agents are sodium perborate and sodium percarbonate.

(4) Other ingredients, predominantly proteolytic enzymes, optical brighteners, perfumes, dyes, foam modifiers, stabilizers, anti-redeposition agents, preferably not, however, CMC, which to a certain extent will be decomposed by the cellulase, in a cumulative total amount of from 0 to 10 percent by weight, typically from 0.1 to 5 percent.

(5) Fillers, in particular sodium sulphate, and water, in such amount as to bring the total of the detergent formulation to 100 percent.

In the brochure "Novo Enzymes" for the detergent industry (B 157a-GB 2000, February 1977), other general examples of detergent formulae, which may be used together with the herein described cellulase preparations, are listed, namely compositions characterized by either specific compounds or categories of compounds and corresponding percentages thereof or corresponding ranges for the percentages thereof.

On page 5 of the Danish Patent Application No. 5691/78, filed on Dec. 12, 1978, some specific detergent compositions, which could be used together with the herein described cellulase preparations, are listed.

In a preferred embodiment of the main wash detergent composition in accordance with the present invention, the harshness reducing agent is present in an amount corresponding to from 2.5 to 100 regular $C_x$ units/g of main wash detergent, or from 1.5 to 60 modified $C_x$ units/g of main wash detergent, preferably from 5 to 50 regular $C_x$ units/g of main wash detergent, or from 3 to 30 modified $C_x$ units/g of main wash detergent. In this way a satisfactory harshness reducing effect can be obtained, and also an excess of cellulase (which would make the overall main wash detergent composition uneconomical) can be avoided.

In a preferred embodiment of the main wash detergent composition in accordance with the present invention, the main wash detergent includes a bacterial proteinase, preferably a proteinase produced by means of *Bacillus lichenformis*, (e.g., ALCALASE). Surprisingly, it has been found that the detergent additives cellulase and proteinase are compatible, and that they each exert a satisfactory effect at the pH values during the washing procedure, even though it might be thought that the proteolytic enzyme would digest the cellulase. This combined detergent additive exerts both a better cleaning effect and a better softening effect when added to the detergent. (The word "ALCALASE" is a Trademark for a Novo enzyme preparation commercially available.) If proteinase and a granulate of cellulase is used, the mixed enzymatic additive can be prepared either by mixing a previously prepared granulate of proteinase with a previously prepared granulate of cellulase or by mixing a concentrate of proteinase with a concentrate of cellulase and then introducing this mixture into a granulating device, together with the usual granulating aids.

In a preferred embodiment of the main wash detergent composition in accordance with the present invention, perborate is one of the detergent ingredients. Under certain conditions, perborate enhances the washing efficiency and it has surprisingly been found that perborate and the cellulase in the main wash detergent composition according to the invention are compatible.

In the third aspect of the present invention there is provision of a main wash method, in which a cellulase containing main wash detergent composition is used as the detergent.

In a preferred embodiment of the main wash method in accordance with the present invention, the fungal cellulase is used in a concentration in the washing solution corresponding to from 10 to 100 regular $C_x$ units/liter washing solution, or from 6 to 60 modified $C_x$ units/liter of washing solution, preferably from 20 to 50 regular $C_x$ units/liter of washing solution, or from 12 to 30 modified $C_x$ units/liter of washing solution.

In a preferred embodiment of the invention the pH in the washing solution is between 7 and 10, preferably between 7, 5 and 9, 5. Hereby the cellulase is able to exert its full activity.

In a preferred embodiment of the main washing method in accordance with the present invention a significant part of the main wash is performed at a temperature below 70° C., preferably below 60° C.

The following examples illustrate the fermentation, by which the harshness reducing agent of this invention is produced (Examples 1, 6 and 8), cellulase containing main wash detergent compositions in accordance with the invention and main wash methods in accordance with the invention (Examples 2–8).

EXAMPLE 1

The strain DSM 1800 was cultivated at 37° C. on an agar substrate with nutrient having the composition:

| | |
|---|---|
| Yeast extract Difco | 4 g |
| $K_2HPO_4$ | 1 g |
| $MgSO_4.7H_2O$ | 0.5 g |
| Glucose | 15 g |
| Distilled water | 1000 g |
| Agar | 15 g |

A primary group of 500 ml shaking flasks was prepared; these shaking flasks contained 100 ml of aqueous substrate with the following nutrient composition:

| | |
|---|---|
| Corn steep liquor | 2.4 percent |
| Glucose | 2.4 percent |
| $CaCO_3$ | 0.5 percent |
| Soy oil | 0.5 percent |

Before the addition of $CaCo_3$ the pH value was adjusted to 5.5 with 4 N NaOH, and sterilization was performed at 121° C. for 20 minutes before use.

After growth for 7 days on the agar slant the spores were transferred to the shaking flasks in the primary group of 500 ml shaking flasks.

A secondary group of 500 ml shaking flasks was prepared; these shaking flasks each contain 100 ml of a substrate with the following nutrient composition:

| | |
|---|---|
| $NH_4NO_3$ | 0.25 percent |
| $KH_2PO_4$ | 0.56 percent |
| $K_2HPO_4$ | 0.44 percent |
| $MgSO_4.7H_2O$ | 0.075 percent |
| Cellulose | 2.0 percent |
| $CaCO_3$ | 0.25 percent |
| Pluronic | 0.01 percent |

Before the addition of $CaCO_3$ the pH value was adjusted to 6.8–7.0 by means of 4 N NaOH, and sterilization was performed by treatment in an autoclave at 121° C. for 20 minutes before use.

After growth for 2×24 hours at 37° C. in the primary group of shaking flasks, inoculation with 6 percent from the primary group of shaking flasks to the secondary group of shaking flasks was performed.

After fermentation in the secondary group of shaking flashs for 140 hours at 37° C. the cellulose activity was 4.2 regular $C_x$ units/ml culture broth. Then the culture broth was purified in the following manner: the culture broth was filtered on distomaceous earth (Hyflo-supercell), the filtrate was concentrated by ultrafiltration, and the retentate was freeze dried. The freeze dried powder (A) showed a $C_x$ activity of 745 regular $C_x$ units/g.

Two additional experiments were carried out in exactly the same manner as described above. After fermentation in the secondary group of shaking flasks for 140 hours the regular $C_x$ cellulose activity in these two experiments was 2.2 and 6.0 $C_x$ units/ml culture broth, respectively. Also, the freeze dried powder in these two experiments showed a regular $C_x$ activity of 558 (powder B) and 518 $C_x$ units/g (powder C).

EXAMPLE 2

In this example the cellulose preparation powder A from Example 1 was used as the harshness reducing agent.

The washing experiment was carried out as a one-step wash with a fully automatic MIELE drum washing machine in accordance with the washing programme called "Kogevask 95° C." indicated in the T-52001 brochure describing the MIELE washing machine type 421 S. The word "MIELE" is a Trademark. The programme called "Kogevask 95° C." has the following approximate temperature-time profile:

| time (min.) | 0 | 6 | 12 | 18 | 24 | 30 | 36 | 42 | 45 |
|---|---|---|---|---|---|---|---|---|---|
| temp. (°C.) | 16 | 27 | 43 | 61 | 76 | 85 | 85 | 82 | flushing with cold water |

The washing solution had the following composition: approximately 16 liters of water with hardness of approximately 20° dH, 5 g/liter of a conventional, commercial powder detergent with the below listed main ingredients (approximate dry solids composition w/w):
- 21% of surfactants (7% of LAS, 11% of soap, and 3% of nonylphenylethoxylate)
- 39% of builders (32% of STPP, 4% of sodium silicate, and 3% of sodium carbonate)
- 26% of sodium perborate
- 13% of sodium sulphate To this washing solution was added the proteolytic enzyme preparation of ALCALASE in a concentration corresponding to 0.06 Anson units/liter of solution. The proteolytic activity of the enzyme preparation was determined according to the modified Anson method, described in Novo Analytical Method No. AF 4.3/5-GB (the original Anson method is described in J. Gen. Physiol., 22, 79–89 [1939]).

To this washing solution was added either nothing more or the cellulase preparation A from Example 1 in a concentration corresponding to approximately 40 regular $C_x$ units/liter of solution.

The test materials used for each of these two parallel experiments were:

(1) 12 pieces of white Terry cloth of cotton with dimensions 42 cm×60 cm, and
(2) 12 pieces of white cotton interlock with the same dimensions.

Furthermore, clean cotton laundry was supplied with the two kinds of test material to provide a total of 3 kg of laundry. The test material was washed 20 times before use with a perborate-containing, conventional detergent using a high temperature programme.

After these 20 repeated washes, simulating washing of the test material in practice, the test material was ready for the washing experiment with or without cellulase.

The test material was washed 6 times with intermediate drying on a line over night. After the final wash, all test pieces (12×2×3) were conditioned on a line in the same room.

The evaluation was performed by a panel consisting of 20 persons. Without knowledge of the identity of the different test pieces, each of the first 10 persons in the panel was asked to make 6 evaluations (that is, 3 for the white Terry cloth and 3 for the white cotton interlock) from which to select the correct statement among the following statements:

(1) The cloth treated with cellulase is softer than the cloth treated without cellulase,
(2) The cloth treated with cellulase has the same degree of softness as the cloth treated without cellulase, and
(3) The cloth treated with cellulase is harder than the cloth treated without cellulase.

3 pieces of test material were selected from the 12 pieces of white Terry cloth of cotton treated with cellulase, and 3 pieces of the test material were selected from the 12 pieces of white Terry cloth of cotton treated without cellulase. These 6 pieces were arranged into 3 pairs, and each of the first 10 members of the panel was asked to evaluate all 3 pairs separately. Similar evaluations were carried out with the white cotton interlock. The remaining 10 persons in the panel were then asked to evaluate the remaining test material in the same way.

Referring only to the white Terry cloth, each person in the panel made 3 evaluations, corresponding to a total from the entire panel of 60 evaluations for this test material.

The white cotton interlock was evaluated in the same manner, the total number of evaluations also being 60 in this case.

The result of the above described evaluation appears in the following Table 1. Table 1 also shows the pH of the detergent solution at the start of the wash, after 10 minutes, and after 20 minutes (t=0, t=10, and t=20, respectively).

EXAMPLE 3

Example 2 was repeated. The results appear in Table 1.

EXAMPLE 4

In this Example the cellulase preparation powder B from Example 1 was used as the harshness reducing agent. Example 2 was repeated, but with the following changes: the washing machine was filled with test material as in Example 2, and then dirty cotton laundry was supplied to provide a total of 3 kg of laundry. The dirty laundry was cotton underwear from a military camp. The results appear in Table 1.

EXAMPLE 5

In this Example the cellulase preparation C from Example 1 was used as the harshness reducing agent. The experiment described in Example 2 was reported, but with the following changes: the washing programme called "Finvask 60° C." in the T-52001 brochure was used. This programme has the following approximate temperature/time profile:

| time (min.) | 0 | 6 | 12 | 18 | 24 | 30 | 36 | 42 |
|---|---|---|---|---|---|---|---|---|
| temp. (°C.) | 16 | 24 | 35 | 47 | 57 | 55 | 54 | flushing with cold water |

The washing solution had a volume of approximately 26 liters. The pH of the washing solution was adjusted slightly with citric acid. The results appear in Table 1.

TABLE 1

| Example | Test material | Evaluation |
|---|---|---|
| Ex. 2 | terry cloth | 73%: softer with cellulase |
| pH at | | 2%: no difference |
| t = 0:10.0 | | 25%: harder with cellulase |
| t = 10:9.8 | cotton | 77%: softer with cellulase |
| t = 20:9.7 | interlock | 8%: no difference |
| | | 15%: harder with cellulase |
| Ex. 3 | terry cloth | 68%: softer with cellulase |
| pH at | | 5%: no difference |
| t = 0:9.9 | | 27%: harder with cellulase |
| t = 10:9.8 | cotton | 78%: softer than cellulase |
| t = 20:9.6 | interlock | 2%: no difference |
| | | 20%: harder with cellulase |
| Ex. 4 | terry cloth | 84%: softer with cellulase |
| pH at | | 3%: no difference |
| t = 0:9.8 | | 13%: harder with cellulase |
| t = 10:9.7 | cotton | 82%: softer with cellulase |
| t = 20:9.6 | interlock | 5%: no difference |
| | | 13%: harder with cellulase |
| Ex. 5 | terry cloth | 93%: softer with cellulase |
| pH at | | 0%: no difference |
| t = 0:8.9 | | 7%: harder with cellulase |
| t = 10:8.8 | cotton | 93%: softer with cellulase |
| t = 30:8.9 | interlock | 2%: no difference |
| | | 3%: harder with cellulase |

EXAMPLE 6

The strain DSM 1800 was cultivated at 37° C. on an agar substrate with the same composition as the agar substrate in Example 1.

300 liters of an inoculation or pre-fermentation substrate with the nutrient composition:

| Corn steep liquor | 2.4 percent |
|---|---|
| Glucose | 2.4 percent |
| $CaCO_3$ | 0.5 percent |
| Soy oil | 0.4 percent |

(whereby the pH value before addition of $CaCO_3$ was adjusted to 5.5 by means of 4 N NaOH) was sterilized at 121° C. for 45 minutes before use.

After growth for 14 days on the agar substrate the spores were transferred to the sterilized 300 l pre-fermentation substrate. Sterile air was passed through the thus-prepared pre-fermentation broth for 49 hours at 37° C. under a pressure of 0.5 atmospheres and at a rate of 300 liters per minute.

350 liters of a main fermentation substrate having the nutrient composition:

| | |
|---|---|
| Corn steep liquor | 10 percent |
| Cellulose | 3 percent |
| $CaCO_3$ | 0.25 percent |
| $NH_4NO_3$ | 0.25 percent |
| $KH_2PO_4$ | 0.56 percent |
| $K_2HPO_4$ | 0.44 percent |
| $MgSO_4$ | 0.08 percent |
| Pluronic | 0.014 percent |

(whereby the pH value before addition $CaCO_3$ was adjusted to 6.8-7.0 by means of 4 N NaOH) was sterilized by boiling at 123° C. for 60 minutes before use. 30 liters of the pre-fermentation broth was transferred to the thus-sterilized main fermentation substrate. Sterile air was passed through the thus-prepared main fermentation broth under a pressure of 0.5 atmospheres and at a rate of 300 liters per minute. pH was kept below 7.0 with addition of $KH_2PO_4$. The fermentation was carried out at 37° C. for 136 hours. At the conclusion of the fermentation the activity was 29 regular $C_x$ units/ml.

The culture broth was purified in the following manner:

The culture broth was filtered on diatomaceous earth (Hyflo-super-cell). The filtrate was concentrated by ultrafiltration, and the retentate (which for the sake of brevity in the following will be referred to as retentate D) was freeze dried.

The freeze dried powder D showed a regular $C_x$ activity of 1316 $C_x$ units/g, and a modified $C_x$ activity of 953 $C_x$ units/g.

Two more fermentations with subsequent ultrafiltrations were carried out in the same way as indicated above. The corresponding retentates are referred to as retentate E and F. Retentate F was freeze dried, and the freeze dried powder F showed a regular $C_x$ activity of 743 units/g and a modified $C_x$ activity of 580 units/g.

The freeze dried powder D was separated in different components by anionic exchange chromatography in the following manner: 100 g thereof was dissolved in 2000 ml of distilled water at 4° C. The pH was adjusted to 7.5 with 1 M "tris". The solution was then applied to a 4000 ml ion exchange column with 100 g of DEAE-Sephadex A-50. FIG. 1 shows the absorbance $OD_{280}$ at 280 nm of the fractions released from the column. The proteins bound to the column were eluted by a NaCl gradient; the NaCl concentration was measured and plotted on FIG. 1 together with the absorbance of the fractions.

The protein containing fractions were pooled as indicated with the brackets on FIG. 1 and the pooled fractions numbered 1 to 5. Pools 1 to 5 were then freeze dried separately.

The freeze dried pools were characterized by the amount of protein, the composition of proteins and the regular $C_x$ activity, vide Table 2. The isoelectric point of the proteins was determined with a LKB multiphoer apparatus.

TABLE 2

| | Protein, g | Total regular $C_x$ units | pI range | Yield protein, % | Yield $C_x$, % |
|---|---|---|---|---|---|
| Starting material | 53.0 | 131600 | 3.5–9.0 | | |
| Pool 1(x) | 8.6 | 47400 | 6–9.0 | 16 | 36 |
| Pool 2 | 0.9 | 1000 | 4–6 | 2 | 1 |
| Pool 3 | 4.8 | 9500 | 4–5.5 | 9 | 7 |
| Pool 4 | 7.1 | 11000 | 3,5–5.5 | 13 | 8 |

TABLE 2-continued

| | Protein, g | Total regular $C_x$ units | pI range | Yield protein, % | Yield $C_x$, % |
|---|---|---|---|---|---|
| Pool 5 | 17.7 | 18600 | 3,5–5 | 33 | 14 |
| | | | Total | 73 | 66 |

(x)(= $AC_x I$ fraction)

Pool 1 contains all the alkaline components, i.e., the proteins which are not bound to the anionic exchange resin at $6.5 \leq pH \leq 7.5$. Thus, the total amount of modified $C_x$ cellulase activity is present in pool 1, which also contains all the cellulolytic activities with pI above 6.0.

In order to evaluate which of the five pools contained the fraction with the highest softening effect the following experiments were carried out.

Cotton terry cloth was prewashed 20 times as described in Example 2. Following this prewash, 10 cm×10 cm (approx. 4 gram) swatches were cut out and marked.

The cellulase treatment was now carried out in a Terg-O-Tometer laboratory washing machine under the following conditions:

Detergent and dosage: as in Example 2, except for cellulase dosage

| | |
|---|---|
| Initial pH: | approx. 9.5 |
| Temperature: | 50° C. |
| Time: | 30 min. |
| Water hardness: | 20° dH |
| Volume per beaker: | 1200 ml |
| No. of swatches per beaker: | 10 |
| Cellulase dosage: | see table below, in all cases 100 mg of the freeze dried pools/liter |

| Dosage: | Pool 1 | Pool 2 | Pool 3 | Pool 4 | Pool 5 |
|---|---|---|---|---|---|
| mg protein/l | 31 | 13 | 28 | 34 | 52 |
| regular $C_x$ units/l | 170 | 15 | 56 | 52 | 55 |
| modified $C_x$ units/l | 170 | 0 | 0 | 0 | 0 |

The evaluation was carried out by a panel consisting of 10 persons, who were given different sets of swatches, each consisting of three swatches, and requested to arrange the swatches within each set according to softness. Each set consisted of two swatches, which were washed with one of the pools, and the swatch served as a control. 9 persons of the 10 persons in the panel found that the swatches washed with pool 1 were softer than the one with no pool added. All the other pools did not significantly soften the swatches.

From the above it may be concluded that pool 1 contains $C_x$ activity which has a softening effect. The $C_x$ activity in the pools 3–5 exhibits no significant softening effect at dosage levels, which normally provide a softening effect.

EXAMPLE 7

Retentate E from Example 6 was spray-dried, whereby a crude concentrate was formed.

This crude concentrate was forced through a screen with a hole diameter of 0.5 mm, thus obtaining a mean diameter of 17.4 μm. The cellulase activity of the concentrate in this condition was 650 regular $C_x$ units/g.

A mixture consisting of

| | |
|---|---|
| The above cellulase concentrate | 2.5 kg |

-continued

| Cellulose powder (Arbocel BC 200) | 1.0 kg |
|---|---|
| TiO$_2$ | 0.2 kg |
| NaCl (particle size <0.2 mm) | 6.1 kg | was mixed in a mixer (Lödige FM 50/1 MZ) at a rotational speed of 120 r/m and a knife speed of 3000 r/m. To the thus produced mixture was added 1 kg of a 20% aqueous solution of polyvinyl pyrrolidon (PVP K 30), whereby the above indicated rotational speed and knife speed was maintained. The addition of the aqueous solution was carried out by means of a pressure nozzle and lasted for 1 minute. This wet mixture then was further treated for 3 minutes in the mixer at a mixing speed of 200 r/m and a knife speed of 3000 r/m. Twice a further amount of water was added, viz. 200 g and 100 g of water, respectively, both times followed by treatment in the mixer of a duration of 3 minutes. It was observed that the temperature in the mass rose from 25° C. to 30° C. during granulation. The moist granulate was dried in a fluid bed to a water content of 1.6%. The words "Lödige" and "Arbocel" are trademarks.

Regular $C_x$ activity of dry granulate:

| Calculated | 164 regular $C_x$ units/g |
|---|---|
| Found | 136 regular $C_x$ units/g |
| Activity loss | 17%. |

This product was a particulate produce with lens shaped particles. For the sake of brevity it will be referred to as granulate E.

Granulate E exhibited the following grain size distribution:

| Particle size, μm | % of particles |
|---|---|
| >1180 | 15 |
| >1000 | 28 |
| >850 | 43 |
| >707 | 62 |
| >600 | 76 |
| >500 | 87 |
| >420 | 94 |
| >300 | 1.8 |
| Mean diameter = 790 μm. | |

Granulate E was coated in the following manner. 4,0 kg of granulate E was dumped into a mixer (Lödige, type M 20E). The mixture was heated to 65° C., and then 160 g of melted polyethylene glycol 4000 (molecular weight 4000) was added; this mixture was mixed for 1 minute. Subsequently, the granulate was powdered with 360 g of TiO$_2$ and 90 g of magnesium silicate. After a mixing time of 5 minutes further 40 g of polyethylene 4000 was poured onto the mixture, and the mixing was continued for 1 minute. The charge was left for cooling. 1 kg of the thus produced coated granulate was dust blown for 1.5 minutes at 65° C. on a fluid bed.

The activity of the granulate appears from the following analysis:

| | Coated granulate | Coated and dust blown granulate |
|---|---|---|
| Activity, Regular $C_x$ units/g | 137 | 138 |

The above indicated coated granulate, the coated and dust blown granulate, and granulate E are typical embodiments of a harshness reducing agent in detergent additive form.

A washing experiment with granulate E was carried out as in Example 6, with the following change:
Cellulase dosage:
333, 667, 1000, 1333, and 1667 mg/liter.

The evaluation was carried out as in Example 6, with the following changes:

Each set of swatches consisted of 2 swatches, namely one swatch washed with detergent solution containing inactivated cellulase, and one swatch washed with detergent solution containing active cellulase. The inactivated cellulase was obtained by preparing a stock solution with 10 g granulate E dissolved in water to 250 ml and heating this solution to 90° C. and maintaining this temperature for 10-15 minutes. A total of 5 sets were evaluated and the results of the evaluations are shown in Table 3 below:

TABLE 3

| | | Softness Evaluation (%): | |
|---|---|---|---|
| | | Cellulase | Inact. Cellulase |
| Set No. | Cellulase dosage (mg/liter) | Evaluation: swatch treated as indicated is softest says: | |
| 1 | 333 | 60% | 40% |
| 2 | 667 | 70% | 30% |
| 3 | 1000 | 70% | 30% |
| 4 | 1333 | 70% | 30% |
| 5 | 1667 | 90% | 10% |

EXAMPLE 8

In this example different strains of *Humicola insolens* were compared, i.e., CBS 14764 (identical to ATCC 22082), DSM 2069, and DSM 2068. These strains were cultivated as described in Example 1, with the exception that the substrate for the secondary group of shaking flasks besides the constituents indicated in Example 1 contained 14% corn steep liquor. Freeze dried powders were produced from the fermentation broths as indicated in Example 1. The freeze dried powders were desalted, redissolved and desalted on a Sephadex G 25 column and freeze dried again. These freeze dried powders exhibited 1096, 480 and 690 regular $C_x$ units/g, respectively. Also a portion of the freeze dried powder F from Example 6 (DSM 1800) was used in this Example.

The freeze dried pool 1 from Example 6 was purified further by cation exchange on CM-Sepharose CL 6B. An amount of this freeze dried pool 1 corresponding to 1.7 g protein was dissolved in a citric acid buffer at pH 5.0 and applied to a 1000 ml column with the cation exchanger, to which the protein was attached. It was eluated with a NaCl gradient, and at a NaCl concentration of 250 mM the pure CMC active AC$_x$I protein was eluated. The molecular weight of this protein is found to be 80,000 by means of SDS gel electrophoresis. Also, this protein was used for preparation of antiserum (rabbits).

This antiserum was now used for quantification of the content of the AC$_x$I protein by means of immunological techniques, i.e., rocket immunoelectrophoresis, as described by B. Weeke in Scandinavian I. Immun., 2 Suppl. 1, page 37 (1973).

The rocket immunoelectrophoresis pattern is shown on FIG. 2. The electrophoresis was performed overnight in a tris maleate buffer of pH 7 and with a voltage gradient of 1.0 Volt/cm.

In FIG. 2 a corresponds to the DSM 2069 product (3 mg/ml), b corresponds to the CBS 14764 product (2 mg/ml), c corresponds to the DSM 2068 product (3 mg/ml) and $d_n$ corresponds to the DSM 1800 product (n mg/ml).

The above indicated cellulase preparations originating from DSM 1800, CBS 14764, DSM 2068, and DSM 2069 were used in the washing experiment described below:

Cotton terry cloth was prewashed 20 times as described in Example 2. Following this prewash, 10 cm×10 cm (approx. 4 gram) swatches were cut out and marked.

The cellulase treatment was now carried out in a Terg-O-Tometer laboratory washing machine under the following conditions:

Detergent and dosage: as in Example 2, except for cellulase dosage

| Initial pH: | approx. 9.5 |
|---|---|
| Temperature: | 50° C. |
| Time: | 30 min. |
| Water hardness: | 20° dH |
| Volume per beaker: | 1200 ml |
| No. of swatches per beaker: | 10 |
| Cellulase dosage: | see table below |

| Cellulase | none | DSM 1800 | CBS 14764 | DSM 2068 | DSM 2069 |
|---|---|---|---|---|---|
| dosage (mg/liter) | 0 | 102 | 39 | 96 | 105 |
| Regular $C_x$ units/liter | | 76 | 43 | 66 | 50 |

The cellulase preparation originating from DSM 1800 was added in a dosage of 76 regular $C_x$ units/liter, and the other cellulase preparations were added in a dosage to generate the same $AC_xI$ protein concentration (determined immunologically as described previously in this Example) in the wash solution as the DSM 1800 preparation. The cellulase treatments were repeated 6 times. After each treatment the swatches were thoroughly flushed in tap water and air dried on a line overnight.

The evaluation was carried out by a panel, consisting of 10 persons, who were given 4 different sets of swatches, each consisting of 3 swatches, and requested to arrange the swatches within each set according to softness. The softest swatch in a set was given a "1", the next a "2", and so on. The composition of the sets evaluated and the results of the evaluations, expressed in percent (the percentage of the panel which places a certain swatch in a certain softness category), are shown in Table 4 below:

TABLE 4

| | | Softness Evaluation (%): | | |
|---|---|---|---|---|
| | | | Softness category | |
| Set No. | Cellulase | "1" softest | "2" | "3" |
| 1 | None | 0 | 10 | 90 |
| | powder C (Ex. 6) | 80 | 20 | 0 |
| | powder from CBS 14764 | 20 | 70 | 10 |
| 2 | None | 0 | 30 | 70 |
| | powder C | 70 | 30 | 0 |

TABLE 4-continued

| | | Softness Evaluation (%): | | |
|---|---|---|---|---|
| | | | Softness category | |
| Set No. | Cellulase | "1" softest | "2" | "3" |
| | (Ex. 6) powder from DSM 2068 | 30 | 40 | 30 |
| 3 | None | 0 | 20 | 80 |
| | powder C (Ex. 6) | 30 | 50 | 20 |
| | powder from DSM 2069 | 70 | 30 | 0 |

We claim:
1. A harshness reducing detergent additive for a main wash detergent composition, comprising
   a non-dusting granulate containing a fungal cellulase producible by a strain of *Humicola insolens* or *Humicola grisea* var. *thermoidea*.
2. A harshness reducing agent according to claim 1, wherein the non-dusting granulate is coated with a whitening agent in combination with a dust binding agent.
3. A harshness reducing agent according to claim 2, wherein the whitening agent is $TiO_2$.
4. A harshness reducing detergent additive for a main wash detergent composition, comprising
   a solution of a fungal cellulase producible by a strain of *Humicola insolens* or *Humicola grisea* var. *thermoidea*, and a non-ionic surfactant.
5. A harshness reducing agent according to claim 2, which additionally contains a thickening agent.
6. A main wash detergent composition, which comprises detergent ingredients and a harshness reducing amount of a fungal cellulase producible by a strain of *Humicola insolens* or *Humicola grisea* var. *thermoidea*, said composition having a pH in a solution of 1 g of the main wash detergent composition in 1 liter of 10° German water in the range of from 7 to 10.
7. A main wash detergent composition according to claim 6, wherein the harshness reducing agent is present in an amount corresponding to from 2.5 to 100 regular $C_x$ units/g of main wash detergent composition.
8. A main wash detergent composition according to claim 7, wherein the harshness reducing agent is present in an amount corresponding to from 5 to 50 regular $C_x$ units/g of main wash detergent composition.
9. A main wash detergent composition according to claim 8, which also contains a bacterial proteinase.
10. A main wash detergent composition according to claim 9, wherein the bacterial proteinase is a proteinase produced by means of *Bacillus licheniformis*.
11. A main wash detergent composition according to claim 10, wherein one of the detergent ingredients is a perborate.
12. A main wash method which comprises:
   washing cellulose containing textiles, at less than 70° C. with a main wash detergent composition having therein a proteolytic enzyme and a harshness reducing agent at a pH in the range of pH 7–10, said harshness reducing agent being a fungal cellulase producible by a strain of *Humicola insolens* (*Humicola grisea* var. *thermoidea*) and being present in a content of from 5 to 50 regular $C_x$ units/gram of detergent composition.
13. A main wash method according to claim 12, wherein washing is carried out at less than 60° C.
14. A main wash method according to claim 12, wherein washing is carried out with from 20–60 regular $C_x$ units/liter of washing solution.

* * * * *